US009142196B2

(12) United States Patent
Cocco et al.

(10) Patent No.: US 9,142,196 B2
(45) Date of Patent: Sep. 22, 2015

(54) LIGHT BOX EFFECT FOR VIEWING DIGITAL RADIOGRAPHIC IMAGES

(71) Applicant: Dental Imaging Technologies Corporation, Hatfield, PA (US)

(72) Inventors: George J. Cocco, Havertown, PA (US); Carsten Franke, Dusseldorf (DE); Michael J. Parma, Chalfont, PA (US); Louis P. Rubinfield, Glenmoore, PA (US); John Steck, Perkasie, PA (US); David A. Sebok, Eagleville, PA (US); Martin Kaplan, Lansdale, PA (US)

(73) Assignee: DENTAL IMAGING TECHNOLOGIES CORPORATION, Hatfield, PA (US)

( * ) Notice: Subject to any disclaimer, the term of this patent is extended or adjusted under 35 U.S.C. 154(b) by 320 days.

(21) Appl. No.: 13/791,355

(22) Filed: Mar. 8, 2013

(65) Prior Publication Data
US 2014/0111535 A1    Apr. 24, 2014

Related U.S. Application Data

(60) Provisional application No. 61/715,688, filed on Oct. 18, 2012.

(51) Int. Cl.
G09G 5/30 (2006.01)
A61B 6/14 (2006.01)
A61B 6/00 (2006.01)
G06F 19/00 (2011.01)
H04N 5/58 (2006.01)

(52) U.S. Cl.
CPC .. *G09G 5/30* (2013.01); *A61B 6/14* (2013.01); *A61B 6/461* (2013.01); *G06F 19/321* (2013.01); *H04N 5/58* (2013.01)

(58) Field of Classification Search
None
See application file for complete search history.

(56) References Cited

U.S. PATENT DOCUMENTS

| 5,790,216 A | 8/1998 | Inbar et al. |
| 6,177,937 B1 | 1/2001 | Stockham et al. |
| 6,279,253 B1 | 8/2001 | Inbar et al. |
| 6,469,717 B1 | 10/2002 | Wineke et al. |
| D567,249 S | 4/2008 | Gunn et al. |

(Continued)

FOREIGN PATENT DOCUMENTS

| JP | 2004012924 | 1/2004 |
| JP | 2007167084 | 7/2007 |
| JP | 2008272473 | 11/2008 |
| JP | 2011141864 | 7/2011 |

OTHER PUBLICATIONS

EP13160046.2 Extended European Search Report dated Jul. 23, 2013 (7 pages).

(Continued)

*Primary Examiner* — Maurice L McDowell, Jr.
(74) *Attorney, Agent, or Firm* — Michael Best & Friedrich LLP

(57) ABSTRACT

Devices for presentation of digital radiographic images. One device includes a memory for storing at least one radiographic image and a computer connected to the memory. The computer includes a processor and a user interface module. The user interface module is configured to generate a graphical user interface and to cause the at least one radiographic image to be displayed on a display in a first mode and in a light box mode that simulates the appearance of a physical light box.

18 Claims, 16 Drawing Sheets

(56) References Cited

U.S. PATENT DOCUMENTS

| | | | |
|---|---|---|---|
| 7,370,284 | B2 | 5/2008 | Andrea et al. |
| D574,387 | S | 8/2008 | Jasinski |
| D612,861 | S | 3/2010 | Lee |
| D624,087 | S | 9/2010 | Anderson et al. |
| D657,367 | S | 4/2012 | Allen et al. |
| D682,306 | S | 5/2013 | DiJulio et al. |
| D689,900 | S | 9/2013 | Edwards et al. |
| 2002/0065684 | A1 | 5/2002 | Schwalb et al. |
| 2002/0068170 | A1 | 6/2002 | Smalley et al. |
| 2004/0068170 | A1 | 4/2004 | Wang et al. |
| 2008/0267467 | A1 | 10/2008 | Sokulin et al. |
| 2010/0128049 | A1 | 5/2010 | Georgiev et al. |
| 2011/0134252 | A1 | 6/2011 | Furukawa |
| 2012/0265557 | A1 | 10/2012 | Schwalb et al. |

OTHER PUBLICATIONS

Office Action from the European Patent Office for Application No. 13160046.2 dated Jul. 8, 2014 (3 pages).

Notice of Preliminary Rejection from the Korean Patent Office for Application No. 10-2013-68317 dated Sep. 23, 2014 with English translation (7 pages).

Surgical PACS Access, Brainlab, retrieved from Internet on Mar. 18, 2013 <URL: http://www.brainlab.com/product/item/surgical-pacs-access>.

First Office Action from the Japanese Patent Office for Application No. 2013087063 dated May 8, 2014 (4 pages).

Canadian Office Action for Application No. 2,819,765 dated Mar. 11, 2015 (5 pages).

LIGHT BOX EFFECT FOR VIEWING DIGITAL RADIOGRAPHIC IMAGES

BACKGROUND

The present invention relates to radiographic imaging, including dental x-ray imaging. More particularly, embodiments of the invention relate to systems for viewing digital radiographic images.

SUMMARY

X-ray and other images are captured or generated using a variety of imaging systems. Although digital imaging technologies have existed for decades, some individuals favor many of the customs associated with film-based image capture and viewing. In particular, in some instances, viewers of x-ray images may find it desirable to view x-ray images in a format resembling the traditional manner of viewing x-ray film images, such as film-based images on a light box (or alternator).

Therefore, embodiments of the invention provide devices for skeuomorphic presentation of digital radiographic images. A light box effect may be considered a type of skeuomorphic effect because the simulated light box imitates an actual light box, which was needed to view x-ray film images, but is not required to view digital images. One device includes a memory for storing at least one radiographic image and a processor connected to the memory. The device includes a user interface module. The device may take the form of a computer and the memory may be internal or external of the computer. The user interface module may take the form of instructions executed by the processor. The user interface module is configured to generate a graphical user interface and to cause the at least one radiographic image to be displayed on a display in a first mode and in a light box mode that simulates the appearance of a physical light box.

Another device includes a memory for storing at least one radiographic image, a computer connected to the memory, and a display connected to the computer. The computer includes a processor and a user interface module. The user interface module is configured to generate a graphical user interface and to display the at least one radiographic image in the graphical user interface in a first mode and to display the at least one radiographic image in the graphical user interface in a light box mode that includes simulated backlighting of the at least one radiographic image. The computer is configured to enter the light box mode in response to one of the group comprising a user input or the output of an ambient light sensor crossing a darkness threshold. The display is configured to display the graphical user interface.

Other aspects of the invention will become apparent by consideration of the detailed description and accompanying drawings.

DETAILED DESCRIPTION

Figure 1:
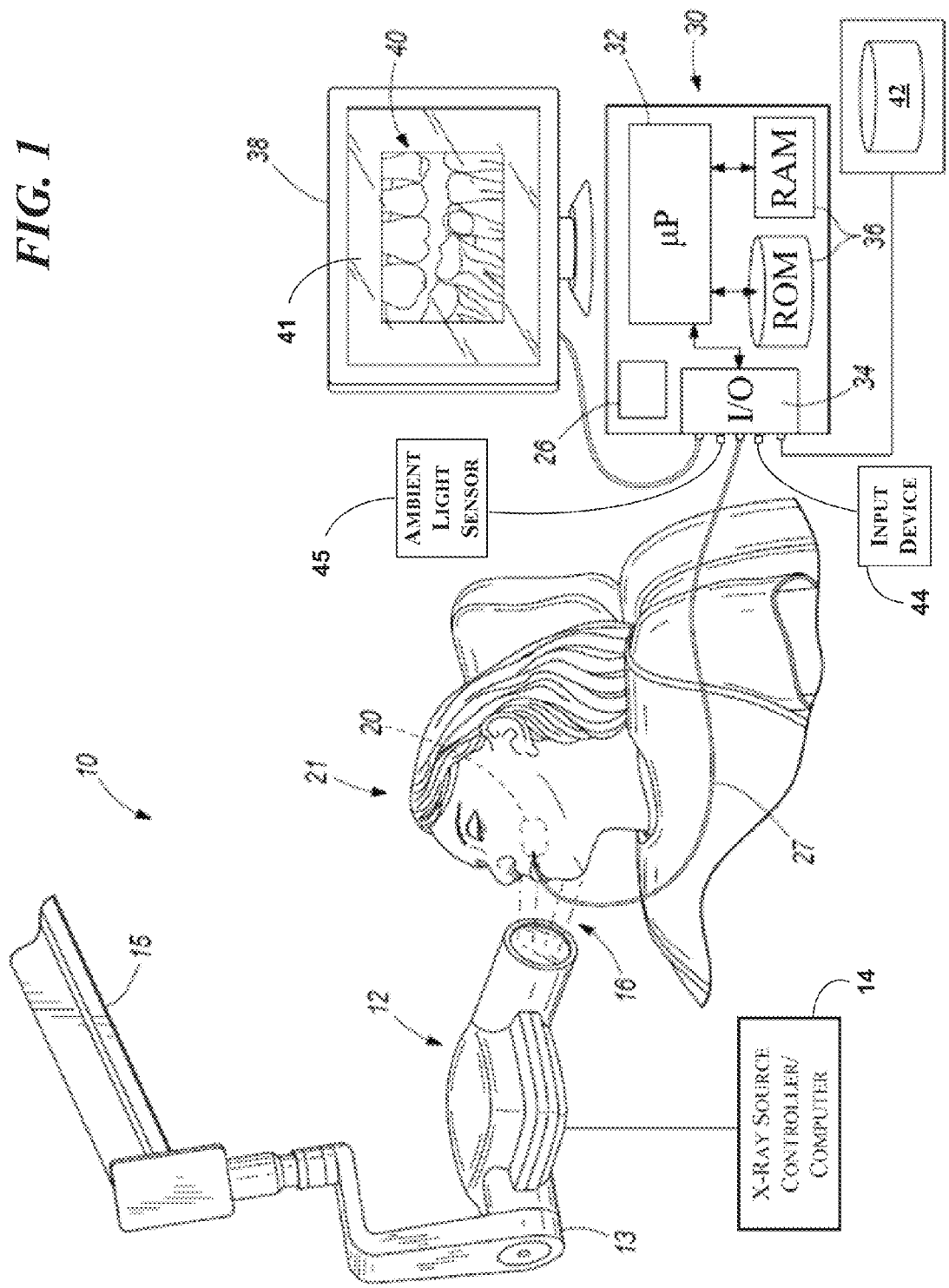
FIG. 1 is a schematic illustration of an x-ray system that generates digital radiographic images.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect. Also, electronic communications and notifications may be performed using any known means including direct connections, wireless connections, etc.

It should be noted that a plurality of hardware and software based devices, as well as a plurality of different structural components may be utilized to implement the invention. Furthermore, and as described in subsequent paragraphs, the specific configurations illustrated in the drawings are intended to exemplify embodiments of the invention and that other alternative configurations are possible.

FIG. 1 illustrates a dental x-ray system 10. The system 10 includes an x-ray source 12. In the embodiment shown, the source 12 is located on an end 13 of a mechanical arm 15. When activated by an x-ray source controller 14, the x-ray source 12 generates an x-ray stream 16 that has a generally circular cross-section. (Of course, x-rays are generally invisible, but a representation of a stream is illustrated to facilitate understanding of the invention.) As shown in FIG. 1, the x-ray source 12 is positioned (e.g., by an operator) so that the x-ray stream 16 is directed to an intraoral receptor 20, which can be, for example, a digital x-ray image detector or computed radiography sensor. The intraoral receptor 20 is shown located in the mouth of a patient 21. In the illustrated embodiment, a wire, cable, or similar connector 27 connects the receptor 20 to a computer 30. However, the receptor 20 could communicate with the computer 30 wirelessly. Alternatively, as discussed in greater detail below, the receptor 20 could include memory for storing image data and, after an imaging procedure, could be removed from the patient's mouth and placed in a reader to retrieve the stored image data.

The computer 30 includes various components, including a user interface module 26, a processor or similar electronic device 32, an input/output interface 34, and memory 36 (e.g., RAM and ROM). In some embodiments, the input/output interface 34 includes a universal serial bus ("USB") connection, and the connector 27 from the intraoral receptor 20 includes a USB cable. Image data captured by the receptor 20 and processed by the computer 30 is sent to a screen 38 coupled to the computer 30 (e.g., through the input/output interface 34 or via a direct, internal connection, such as in a laptop computer, a tablet computer, or a smart phone or similar device). In particular, the computer 30 uses the received image data to generate a digital image 40. The user interface module 26 generates a graphical user interface ("GUI") 41 for displaying the image 40, and the user interface module 26 transmits the GUI 41 and the image 40 to the screen 38. It should be understood that image 40 illustrated in FIG. 1 drawn more distinctly than an x-ray image would typically appear. In some embodiments, the computer 30 stores image data (e.g., the image 40) to the memory 36, a database 42 external to the computer 30, or a combination thereof.

In some embodiments, the screen 38 is a touch screen that is sensitive to a user's touch. Therefore, the touch screen allows a user to directly interact with the GUI 41 on the screen 38. In other embodiments, a user may use one or more input devices 44, such as a keyboard, mouse, joystick, etc., to interact with the GUI 41 on the screen 38. It should be understood that the terms "tap," "touch," "click," and "select" are used interchangeably within the present application to indicate a user selection (e.g., a cursor-control action) on the screen 38 made through a touch screen or with one or more input devices 44. In either embodiment, the screen 38 or device 44, as the case may be, is configured to generate an output or signal in response to a user touching a portion of the screen 38 or using a mouse or similar input device 44 to click on a portion of the screen 38.

In some embodiments, the screen 38 and the computer 30 are included in a tablet-type computer or smart phone.

In some embodiments, an ambient light sensor 45 is also coupled to the computer 30 (e.g., through the input/output interface 34). As described in more detail below, the user interface module 26 uses information from the ambient light sensor 45 to determine when to change a display mode of the GUI 41 from a first or default mode to a light box mode.

It should be understood that the x-ray system 10 illustrated in FIG. 1 is an example of imaging systems that provide a source of images. Other imaging systems in which a series of images is generated could be used with the GUI 41. For example, an extraoral x-ray system could be used to generate images. In addition, an image plate that stores collected image data during a procedure and an associated plate reader could be used in place of the intraoral receptor 20. Furthermore, a surface area scanner (e.g., a laser scanner) that generates a three-dimensional image of a patient's teeth could be used in place of or in addition to the receptor 20. It should also be understood that although the system 10 illustrated in FIG. 1 is used to capture images of a patient's mouth or teeth, the system 10 (and, in particular, the GUI 41) can be used to capture and display images of one or more parts of a human body or animal body other than teeth. Furthermore, in some embodiments the system 10 includes multiple computers. A first computer is configured to receive image data, process the data, and store the data for later access. A second computer (e.g., a tablet computer or smart device) is configured to access the image data (e.g., over a network) and display image(s) 40 within the GUI 41 based on the accessed data.

Figure 2:
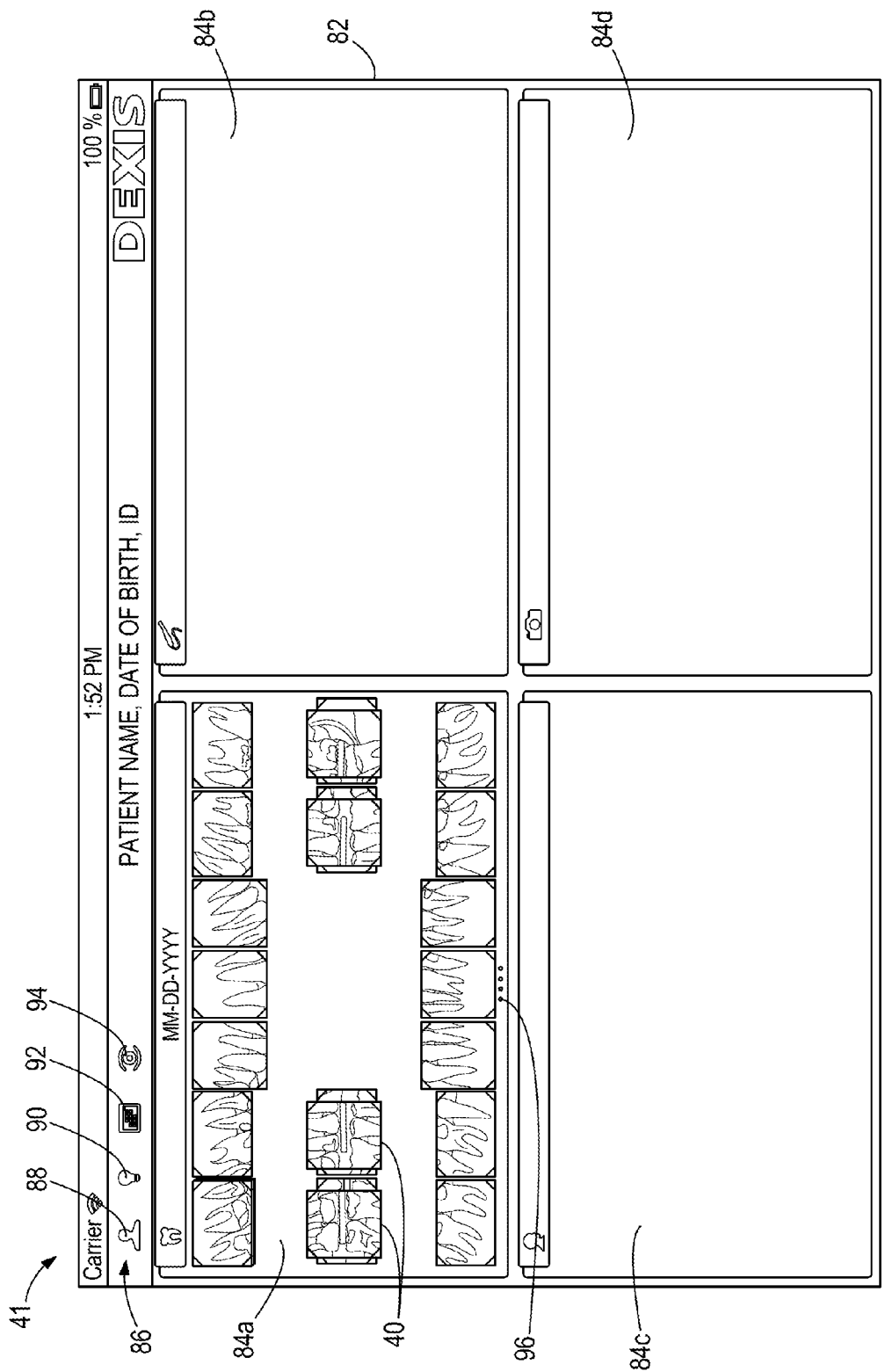
FIG. 2 illustrates a graphical user interface.

The user interface module 26 generates outputs (e.g., changes to the appearance of the GUI 41) in response to input or commands received from a touch screen or one or more input devices 44. As illustrated in FIG. 2, the GUI 41 includes a window 82. The window 82 includes one or more sections or panes 84 for displaying one or more digital images 40. In some embodiments, the window 82 includes four panes 84a, 84b, 84c, and 84d. Pane 84a is an intraoral pane that displays images 40 captured using an intraoral imaging sensor (e.g., the intraoral receptor 20). Pane 84b is a scanner pane that displays images 40 captured using a surface area scanner (e.g., a handheld device manually moved over a patient's teeth to capture image data). Pane 84c is an extraoral pane that displays images 40 captured using an extraoral imaging system. Pane 84d is a camera pane that displays images 40 captured by a camera (e.g., a digital still camera) of a patient's teeth from outside of the patient's mouth. When an imaging procedure (performed at one visit or across multiple visits) collects images from one or more of an intraoral imaging system, a surface area scanner, an extraoral imaging system, and an external camera, the resulting images 40 are displayed within their respective panes 84. Accordingly, a user can use the GUI 41 to view images 40 collected for a particular patient 21 from various sources or systems.

The GUI 41 also includes a menu bar 86. The menu bar 86 displays information regarding the patient associated with the images 40 displayed in the GUI 41 (e.g., patient name, date of birth, identification number, etc.). The menu bar 86 also includes one or more buttons that a user can select (e.g., by touching the screen 38 or using an input device 44) to modify information displayed in the GUI 41. For example, the menu bar 86 illustrated in FIG. 2 includes a patients button 88, a light box toggle button 90, a mouth view button 92, and a history button 94. A user can select the patients button 88 to view a list of available patients. The user can select a listed patient to view images 40 associated with the patient. As described in more detail below, a user can select the light box toggle button 90 to turn on and turn off a light box effect generated within the GUI 41.

The mouth view button 92 allows a user to view images representing a patient's entire mouth or set of teeth. For example, as illustrated in FIG. 2, the pane 84a includes eighteen images representing a full scan of a patient's teeth. A user can select the history button 94 to chronologically view images captured for a selected patient. In some embodiments, when chronologically viewing images for a selected patient, the panes 84 indicate the date that the currently-displayed image(s) were captured (e.g., "Aug. 12, 2012," as illustrated in pane 84a of FIG. 2). A user can "swipe" a pane 84 (e.g., by moving their finger horizontally across the screen 38 displaying the pane 84) to sequentially move through images collected for a selected patient over different dates. In some embodiments, an indication 96 on the bottom of the pane 84 illustrates the number of different dates associated with a particular patient. The indicator 96 can also indicate the location of the currently-displayed images within the chronological listing of dates. For example, the indicator 96 illustrated in FIG. 2 indicates that there are images from four different dates available for the selected patient (four circles are provided). The indicator 96 in FIG. 2 also indicates that the currently-displayed images are associated with the first date of the four dates (the first of the four circles is highlighted). It should be understood that in some embodiments a user can use an input device 44, such as a mouse, to move through images from different dates (e.g., by selecting a portion of the indicator 96 or selecting a "NEXT" or "PREVIOUS" button displayed in the GUI 41) (not shown).

In some embodiments, when a user views images chronologically, a pane 84 displays images from multiple visits, but highlights images within the pane 84 that are associated with a visit (e.g., a dental visit) that the user is currently interested in (i.e., images from the date displayed at the top of the pane 84). As illustrated in FIG. 2, the GUI 41 can highlight the images by displaying the images with a different brightness, contrast, or opacity than images associated with other visits (i.e., associated with other dates than the date displayed in the pane 84). For example, the GUI 41 can display images from other visits with a reduced contrast or modified opacity and a modified brightness and can display images from a currently-selected visit with normal brightness and opacity and full contrast. In some embodiments, (e.g., when the user is not viewing images chronologically) a user can manually select one or more images displayed within a particular pane 84, and the GUI 41 can similarly highlight the manually-selected images. In some embodiments, the GUI 41 only highlights particular images in a pane 84 when the GUI 41 displays images in a light box mode as described below.

When a user selects a button included in the menu bar 86, the user interface module 26 modifies the button, such as by highlighting or un-highlighting the button to indicate the current status or availability of the button. For example, as illustrated in FIG. 2, the history button 94 is highlighted to indicate that the images displayed in the GUI 41 are currently being provided in chronological order. Similarly, as illustrated in FIG. 2, the light box toggle button 90 is not highlighted to indicate that the images displayed in the GUI 41 are not currently being displayed in a light box mode.

Figure 3:
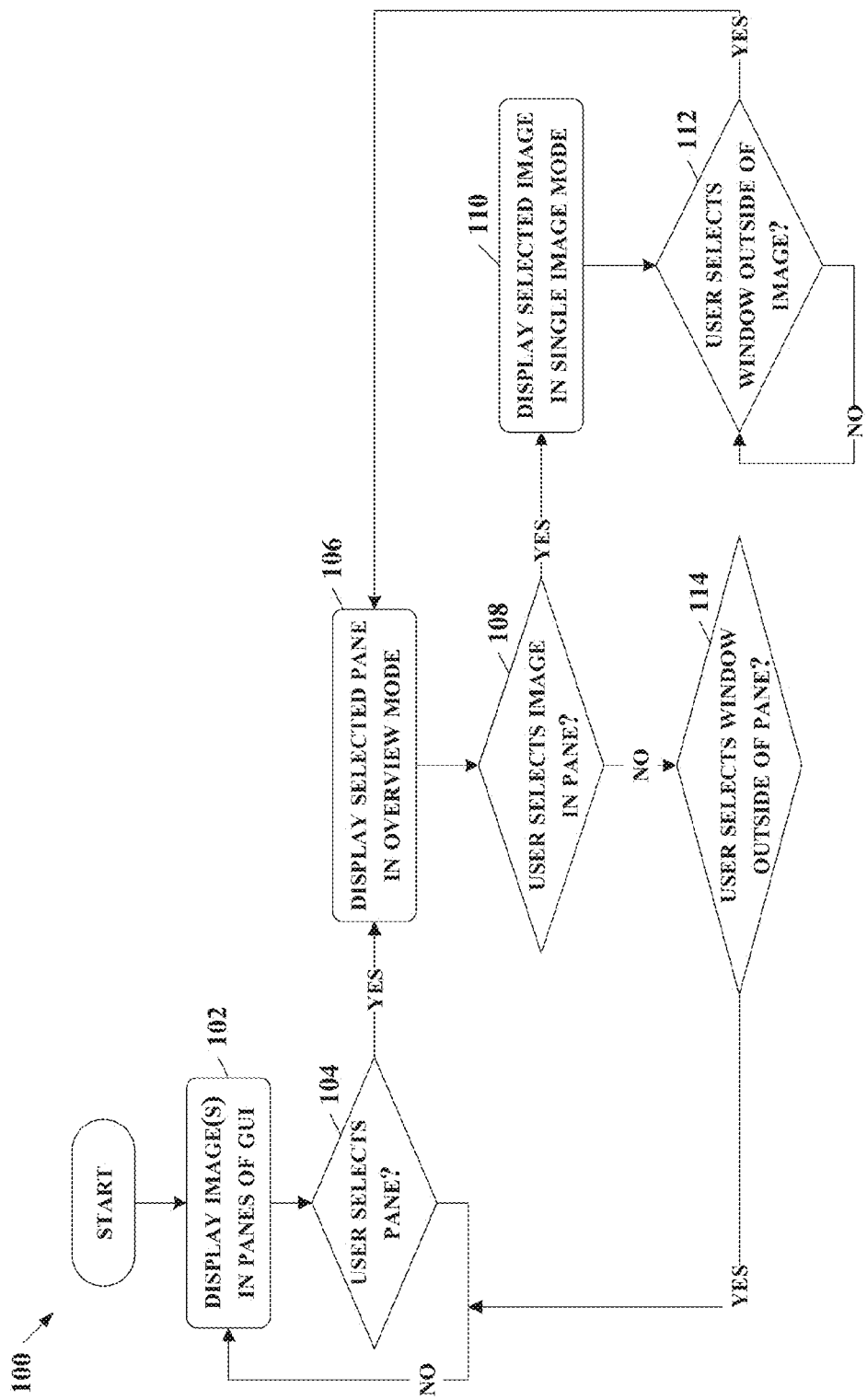
FIG. 3 is a flow chart illustrating a method of displaying images in an overview mode and a single image mode within the graphical user interface of FIG. 2.
Figure 4:
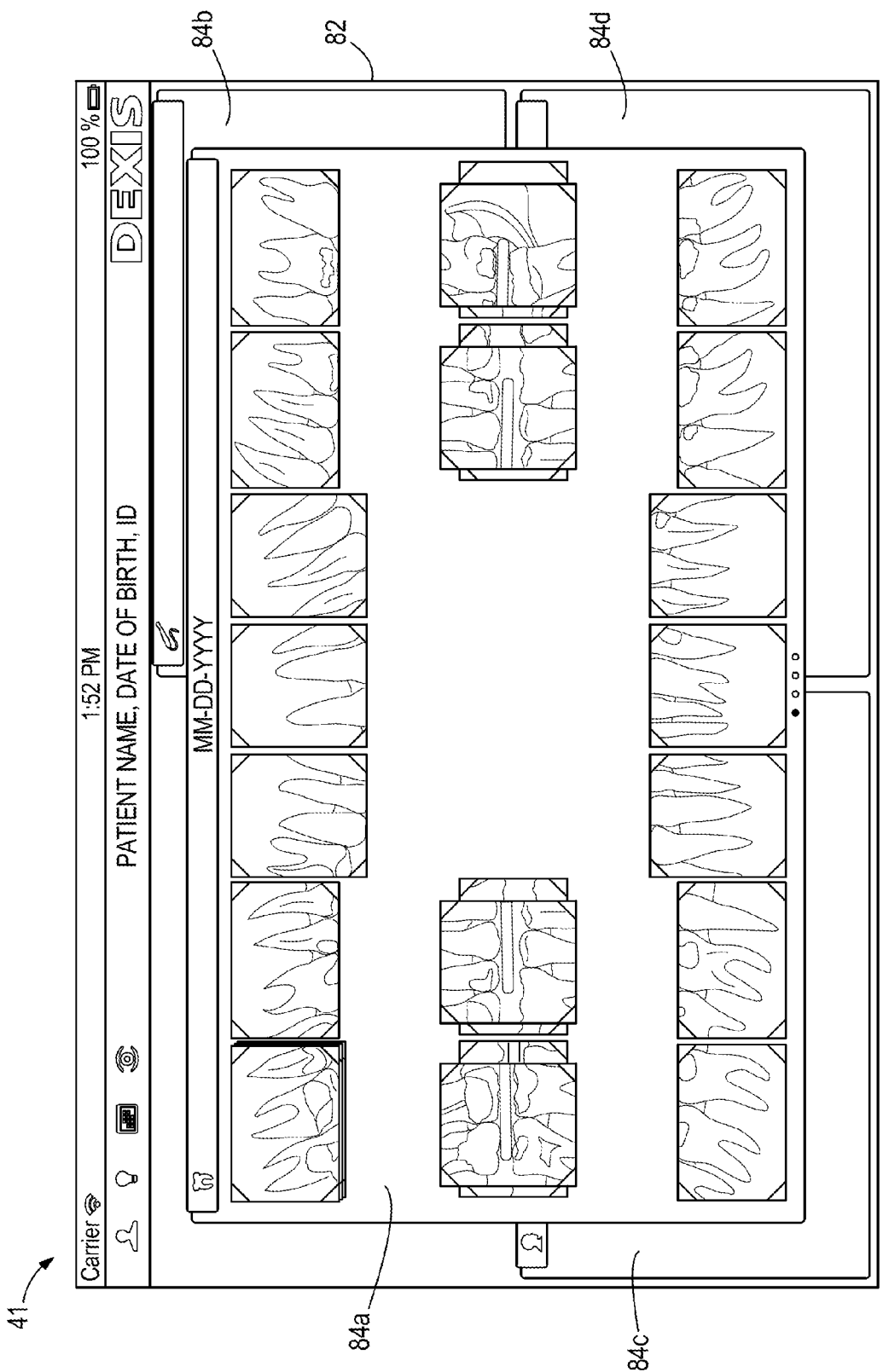
FIG. 4 illustrates the graphical user interface of FIG. 2 displaying images in an overview mode.

FIG. 3 is a flow chart illustrating a method for displaying images 40 within the GUI 41. In particular, FIG. 3 illustrates a method 100 for displaying images 40 within the GUI 41 in an overview mode and a single image mode. As illustrated in FIG. 3, the method 100 starts with displaying one or more images 40 in the GUI 41 in one or more of the panes 84 (at 102). If a user selects a particular pane 84 (e.g., by tapping the pane 84 or selecting the pane 84 with an input device 44) (at 104), the user interface module 26 displays the selected pane 84 in an overview mode (at 106). In the overview mode, the GUI 41 displays the selected pane enlarged or zoomed (e.g., full screen). As illustrated in FIG. 4, the zoomed pane 84a presents a user with an overview of the images 40 obtained for a patient 21 using a particular imaging system (e.g., a series of images associated with a full-mouth intraoral x-ray procedure) full screen. As illustrated in FIG. 4, in the overview mode, the user interface module 26 displays the selected pane 84a in the window 82 in front of the other panes 84b, 84c, and 84d.

Figure 5:
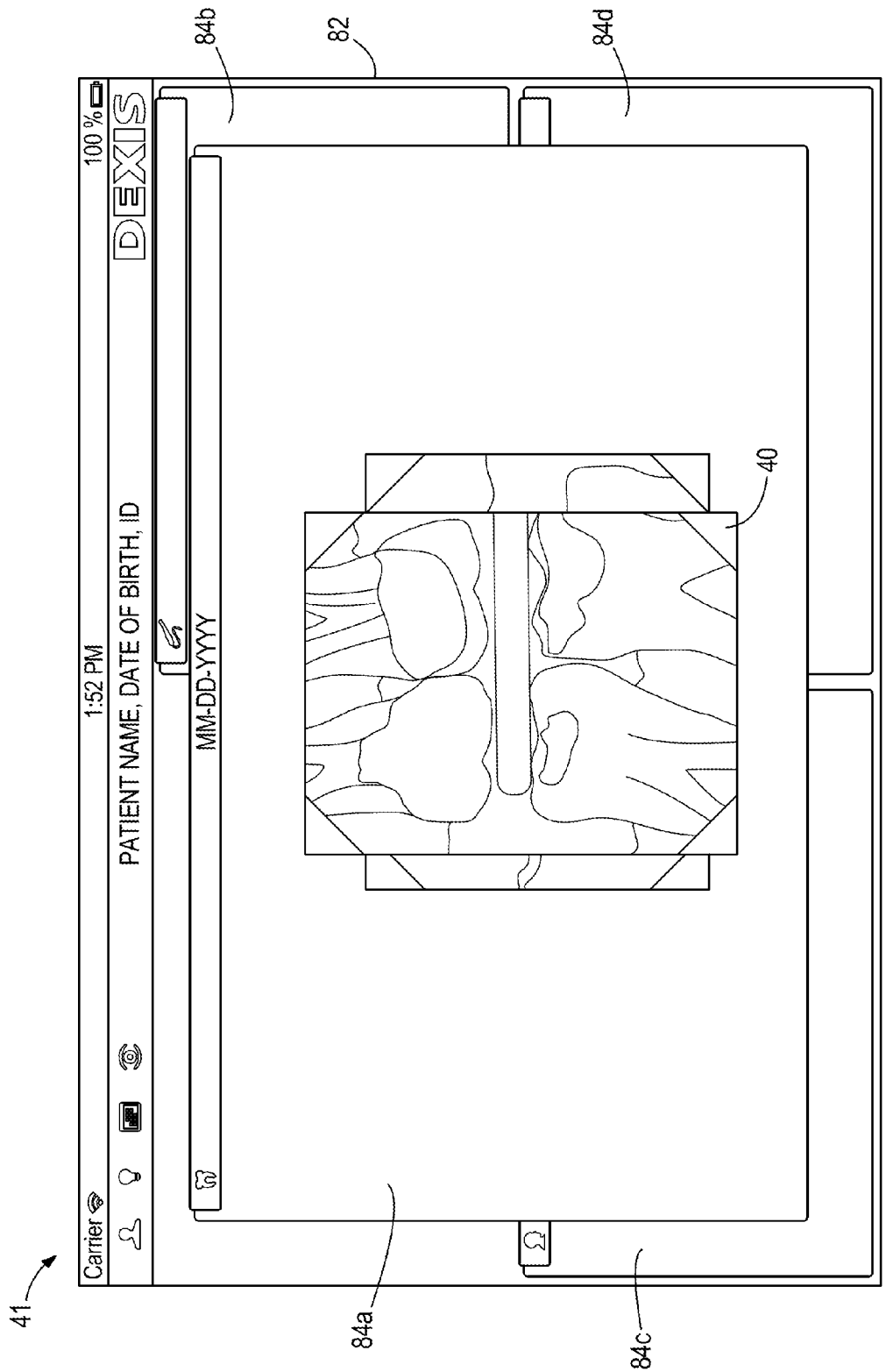
FIG. 5 illustrates the graphical user interface of FIG. 2 displaying images in a single image mode.

If a user selects one of the images 40 within the zoomed pane 84 (at 108), the user interface module 26 displays the selected image 40 within the GUI 41 in a single image mode (at 110). As illustrated in FIG. 5, in the single image mode, the user interface module 26 displays the selected image 40 zoomed in the window 82 within the previously-selected pane 84. To return to the overview display mode, a user can tap within the window 82 but outside of the zoomed image 40 (at 112). Similarly, to exit the overview mode, a user can tap within the window 82 but outside of the zoomed pane 84 (at 114).

In some, but not all, embodiments, the overview mode and the single image mode are only available as sub-modes of the light box mode. In particular, as noted above, the light box toggle button 90 allows a user to turn on and turn off a light box effect generated within the GUI 41. The light box effect simulates a light box presentation of film-based images. In particular, with an actual light box, the light box acts as the source of light and one or more x-ray images on photographic film or other transparency media are placed against the light box. The film acts as an optical filter that alters the light from the light box. Therefore, the image seen by an observer results from the combined effects of the light box and the film. As described in more detail below, to simulate a light box presentation, the GUI 41 displays a bright region partially or completely surrounding at least one digital radiographic image 40 displayed within the GUI 41 to provide a backlighting effect of the displayed digital image 40. Therefore, the GUI 41 provides the light box effect as a type of skeuomorphic effect because the simulated light box imitates an actual light box, which historically was needed to view x-ray images on physical film, but is not required to view digital images.

Figure 6:
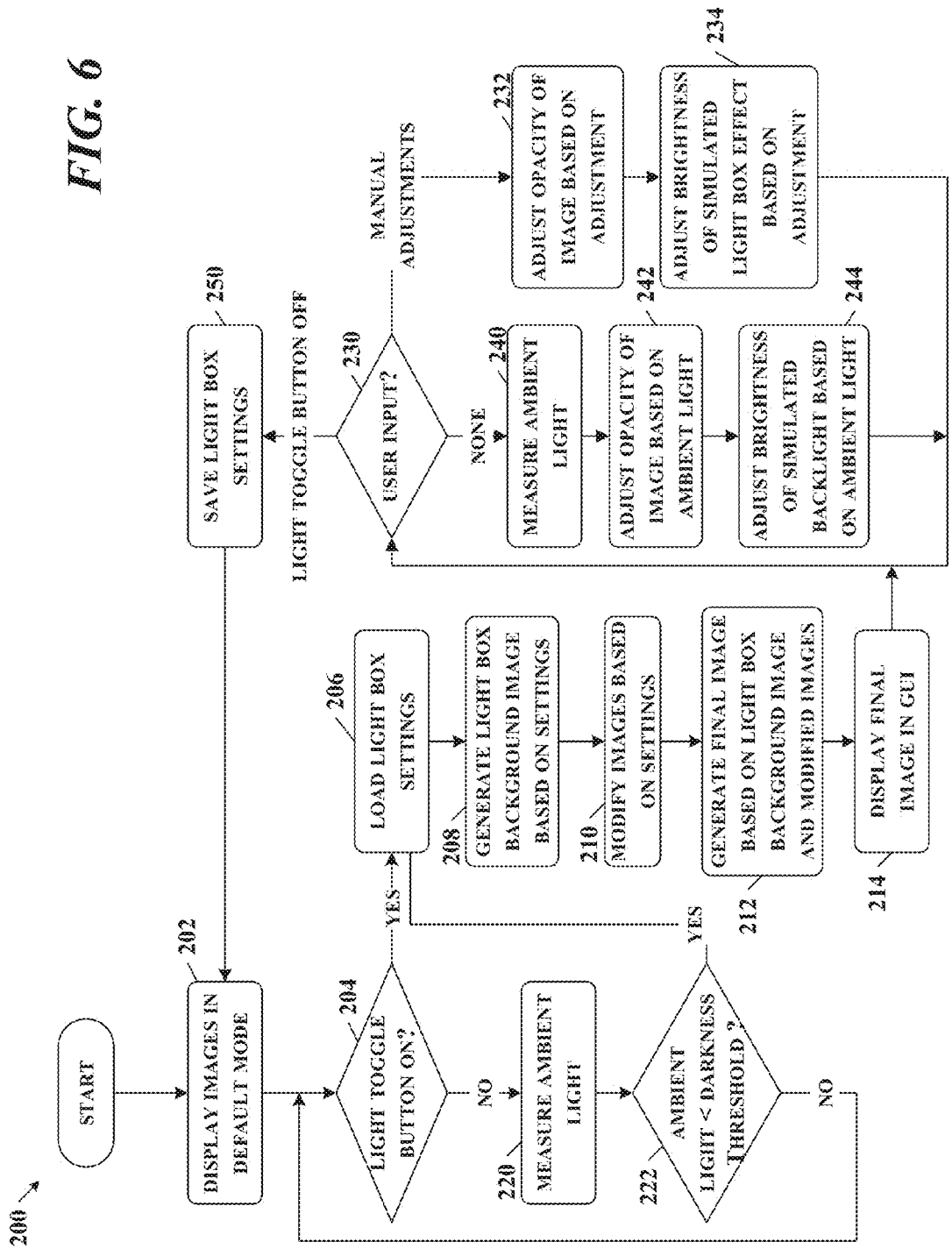
FIG. 6 is a flow chart illustrating a method of displaying images in a default mode and a light box mode within the graphical user interface of FIG. 2.

FIG. 6 is a flow chart illustrating a method 200 for displaying images 40 within the GUI 41 in a first or default mode and a second or light box mode. As illustrated in FIG. 6, the method 200 starts with displaying one or more images 40 in the GUI 41 in one or more of the panes 84 in a first or default mode (at 202). FIGS. 2 and 4-5 illustrate images 40 displayed in the default mode. As illustrated in these figures, in the default mode, images 40 are displayed partially or completely surrounded by a dark region. A user can turn on the light box effect by selecting the light box toggle button 90 (at 204). When the user turns on the light box effect, the user interface module 26 obtains models or settings for simulating the light box presentation (at 206). The settings can include various parameters of the light box effect. Actual light boxes generally are designed with the goal of providing a source of light over a substantially rectangular area that has uniform brightness and spectrum (i.e., color) and is highly diffused. Actual light boxes never achieve this ideal presentation environment and deviate from this ideal environment in different ways. For example, some actual light boxes generate light that is brightest at the center of the box and progressively less bright at points located away from the center, with the dimmest light being at points farthest from the center of the box. Some users may prefer that the simulated light box effect deviate from the ideal environment in similar ways as an actual light box. Other users may prefer that the light box effect comes as close as possible to the ideal presentation environment. Therefore, the user interface module 26 can use the settings for the light box effect to generate a simulated light box presentation that accommodates users preferences. For example, the settings can include a particular non-uniformity in intensity factor for the simulated light box effect (e.g., bright in the center with decreasing brightness moving away from the center). The settings can also specify whether the simulated lighting effect should resemble a hot light. A hot light is a small, bright light placed behind x-ray film to brightly illuminate a small area of the film. A hot light is useful for viewing darker portions of an image. If the settings indicate a simulated hot light, the user interface module 26 generates the light box effect that resembles using a hot light effect to view film-based images (e.g., brightly displaying a small region of the image while keeping the rest of the image substantially darker).

In some embodiments, a user can select one or more of the settings (e.g., through the GUI 41). Settings can be specified for the computer 30 in general or can be associated with particular users of the computer 30. Therefore, in some embodiments, the user interface module 26 uses a known identity of the user to load user-specific settings for the light box effect. The settings can also include settings specific to the screen 38. For example, the settings can include a correction factor that compensates the light box effect based on the parameters of the specific screen 38 used to display the GUI 41.

Figure 7:
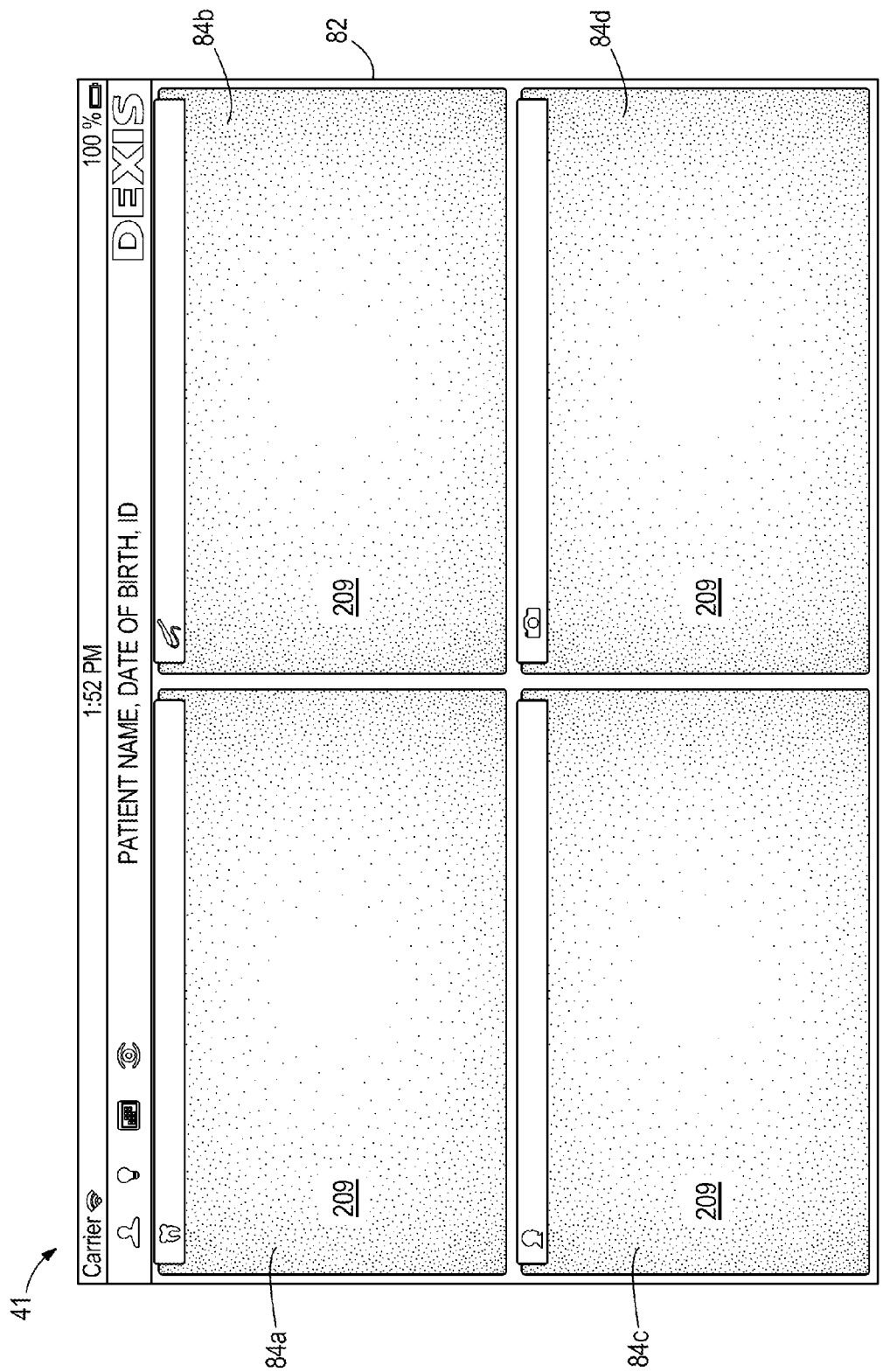
FIGS. 7-12 illustrate the graphical user interface of FIG. 2 displaying images in a light box mode.
Figure 8:
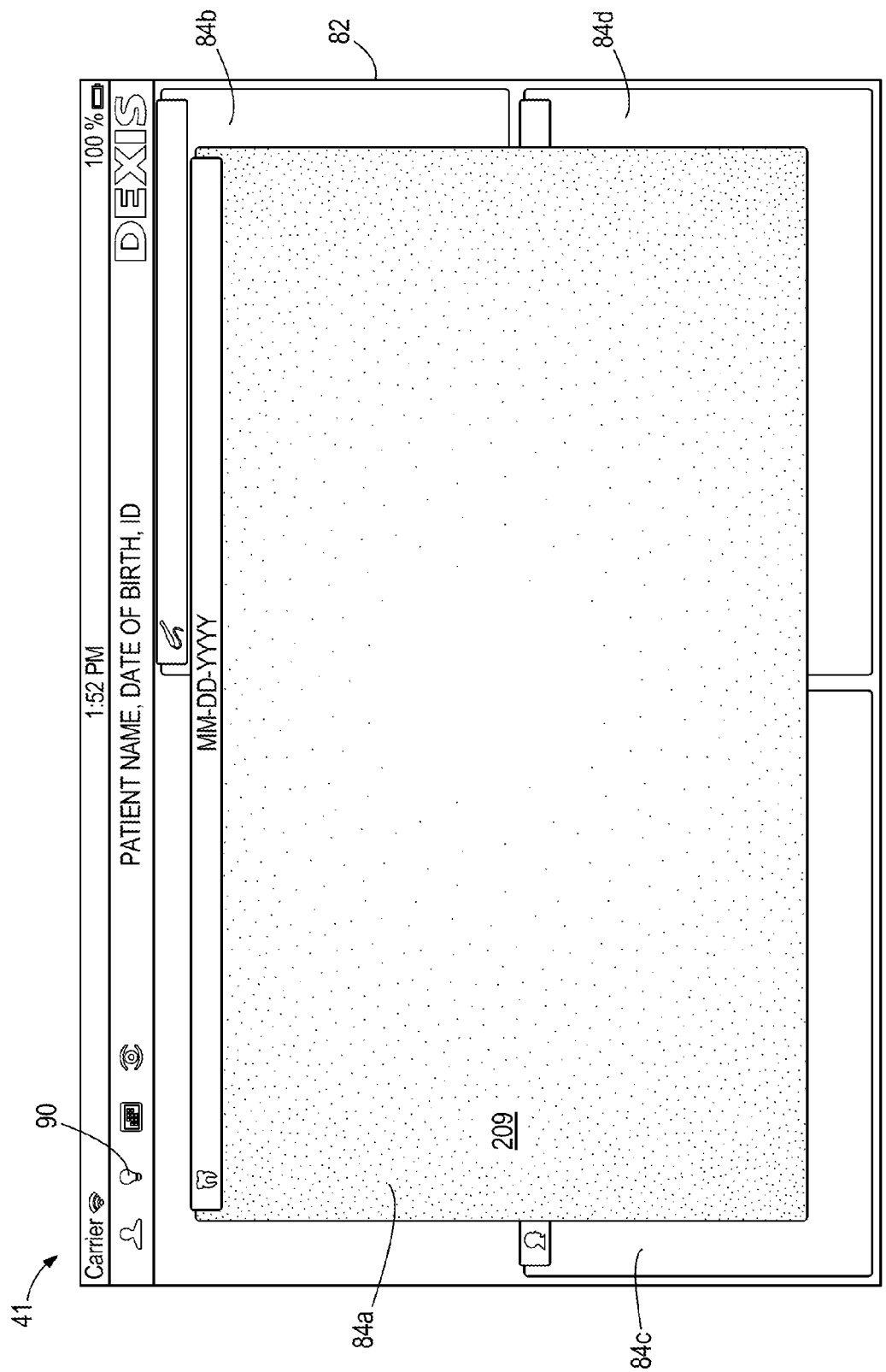

Based on the settings, the user interface module 26 generates (e.g., mathematically) a light box effect background image 209 for one or more of the panes 84 (at 208) (see FIGS. 7-8). The background image 209 is typically a rectangular color image. Color images generally have 3 channels: red, green, and blue. Sometimes, an extra channel is added, called "alpha." The alpha channel can be used for a variety of purposes. One such purpose is to control the opacity or transparency of the image 209. Because the light box effect provides an approximately white light effect, the red, green, and blue values of each pixel are approximately equal to each other.

After generating the background image 209, the user interface module 26 modifies the digital images 40 that will be displayed with the background image 209. In particular, as described in more detail below, the user interface module 26 can modify a digital image 40 in various ways to make the digital image 40 more closely resemble a film-based image when displayed with the background image 209. For example, in some embodiments, the user interface module 26 mathematically treats an image 40 as a filter, which resembles film.

Figure 13:
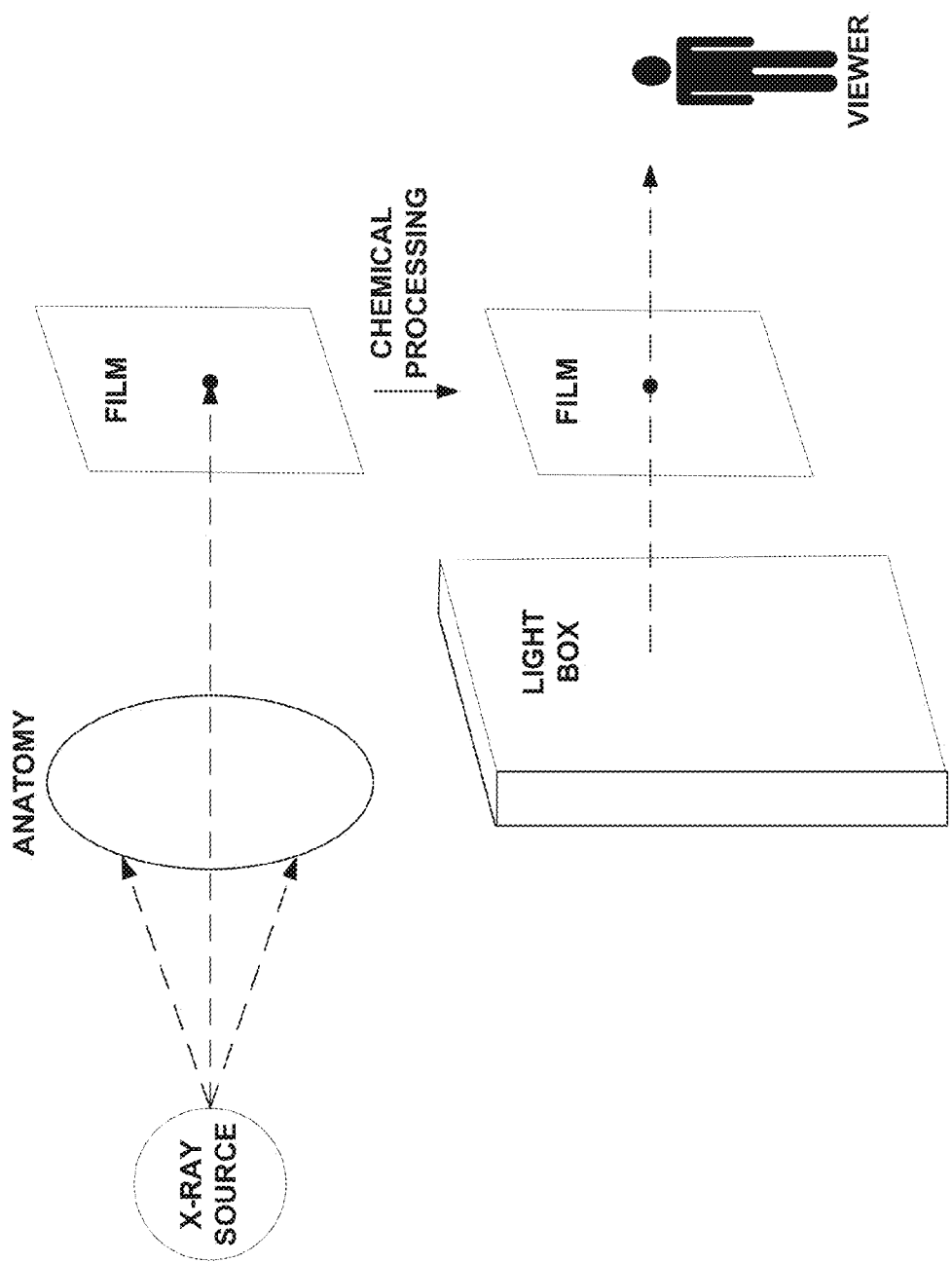
FIG. 13 schematically illustrates a process of exposing, developing, and viewing radiographic film FIG. 14 schematically illustrates a process of capturing and viewing a digital radiographic image.

When actual film is used, an x-ray source generates x-rays that pass through the patient's anatomy. The x-rays expose the film either directly or with the assistance of phosphor screens that convert x-rays to visible light. The film is then developed (chemically processed). The developed film has image-wise varying optical density D that is related to the exposure of the film through a "D log E" curve in traditional film jargon (see FIG. 15), which may be mathematically represented as the function $D_p=D(E_p)$, where $E_p$ is the exposure at pixel position p on the film and $D_p$ is the resulting optical density at pixel position p. The shape of the function $D(E_p)$ is determined by the characteristics of the radiographic film and the chemical processing using during development of the film. Optical density may alternatively be described in terms of transparency $T_p$ of the film, using the relationship $D_p=-\log(T)_p$, or equivalently, $T_p=e^{-D}$. FIG. 16 illustrates the "D log E" curve recast as a "T log E" curve, $T_p=T(E_p)$. When actual film is viewed on an actual light box, as shown in FIG. 13, the light box acts as a source of light, and the film placed against the light box acts as a filter, modifying the light from the light box. The filtered light is observed by the viewer. The viewer sees brightness $P_p=B_pT_p$, where $B_p$ is the brightness of the light box (before passing through the film) at pixel position p, and $O_p$ is the observed brightness (after passing through the film) at pixel position p. It is to be understood that D, $D_p$, $E_p$, $T_p$, $O_p$, and $B_p$ are all implicitly functions of the wavelength of light, i.e., these quantities are spectrally colored.

Figure 14:
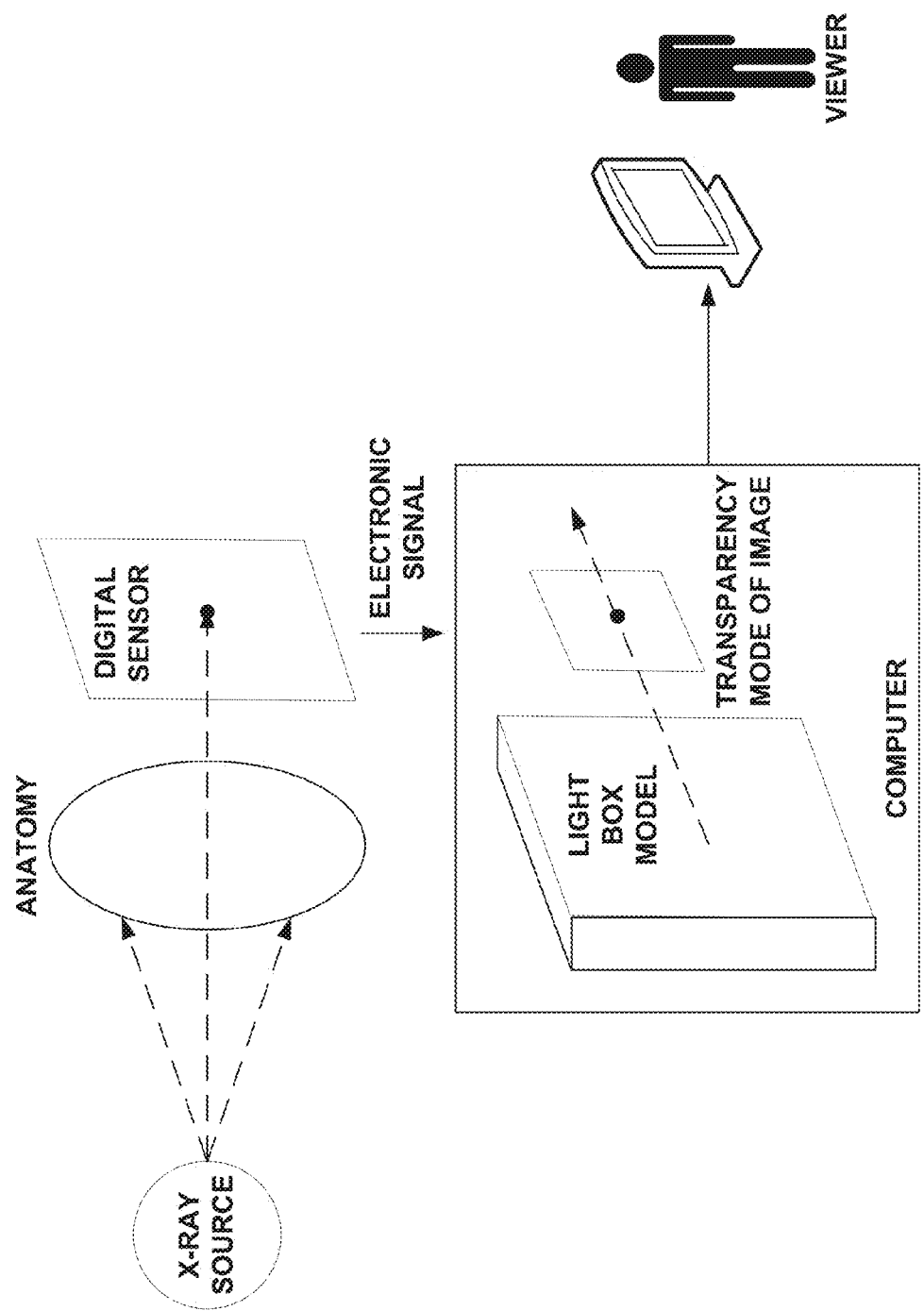

The digital display, such as 41, may mimic film on a light box. FIG. 14 shows the digital x-ray process. As with film, x-rays from a source pass through patient anatomy. However, instead of exposing film, the x-rays expose a digital sensor. The sensor signal at pixel position p is $S_p=S(E_p)$. Often the function S is approximately linear over the range of exposure of interest. When accurately mimicking film on a light box, the brightness of the digital display is modified by the function $B'_p=\alpha B_p$, where the constant $\alpha$ is a scaling factor that allows the digital display to be dimmer (or brighter) than the actual light box being imitated, which imitates a dimmer (or brighter) light box. In particular, many digital displays have a maximum brightness less than many light boxes, which can be accommodated by selecting a suitable scaling factor $\alpha$. The digital display should present brightness $O'_p=B'_pT(S)^{-1}(S)_p$ at pixel position p on the film, where $(S)^{-1}$ is the inverse of the function S (which is the response of the digital sensor to x-ray exposure). Note that $O'_p$ mimics the tone scale of the film. In areas of the displayed image 41 intended to be bare light box between x-ray images, the display brightness should be $B'_p$.

Digital displays have their own tone scale. In particular, brightness is a function of the input code value according to some function $B'_p=\Gamma(\vec{C}_p)$, where $\vec{C}_p$ is a vector of code values for pixel p, typically a 3-element vector with elements for red, green, and blue. Accordingly, the code values to be sent to the digital display are $\vec{C}_p=\Gamma^{-1}(B'_p)$ or $\vec{C}_p=\Gamma^{-1}(O'_p)$ according to whether pixel position p is at a position on the display representing bare light box or film.

Figure 15:
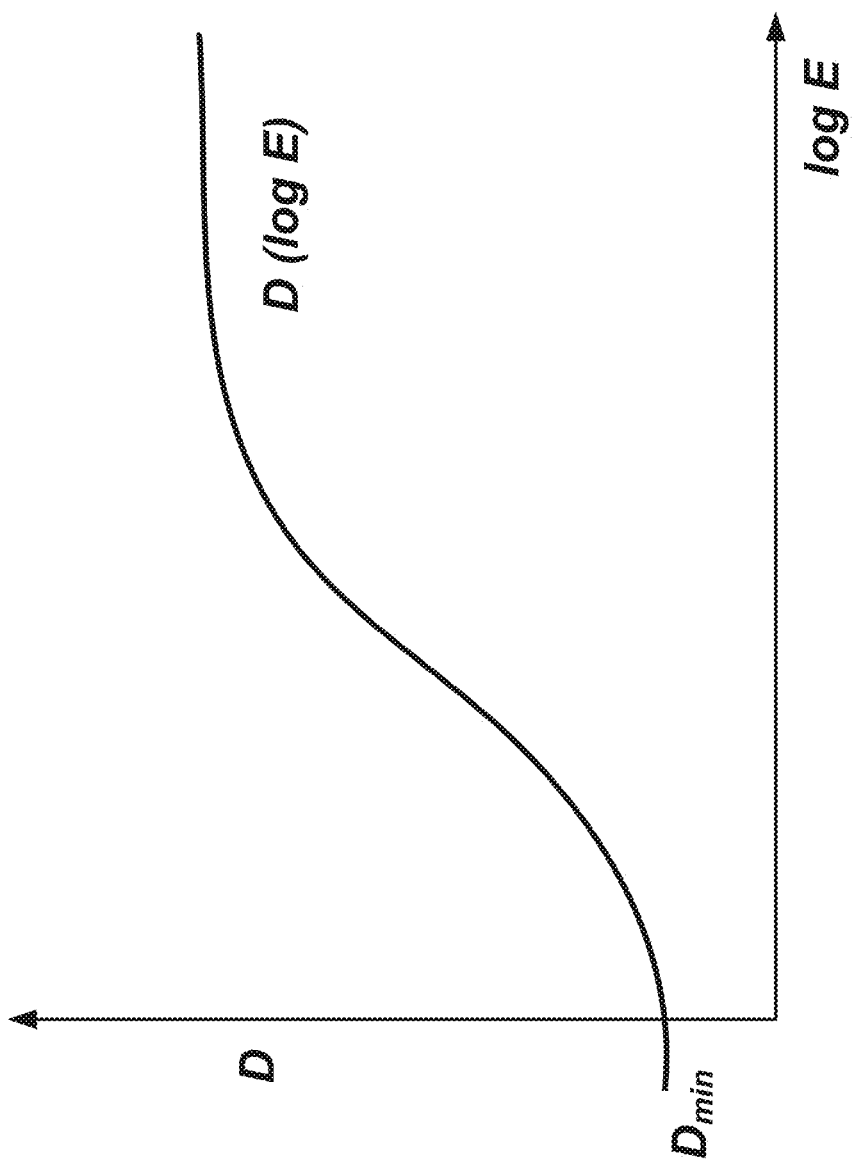
FIG. 15 is a graph representing the density of film as a function of exposure to x-ray radiation.
Figure 16:
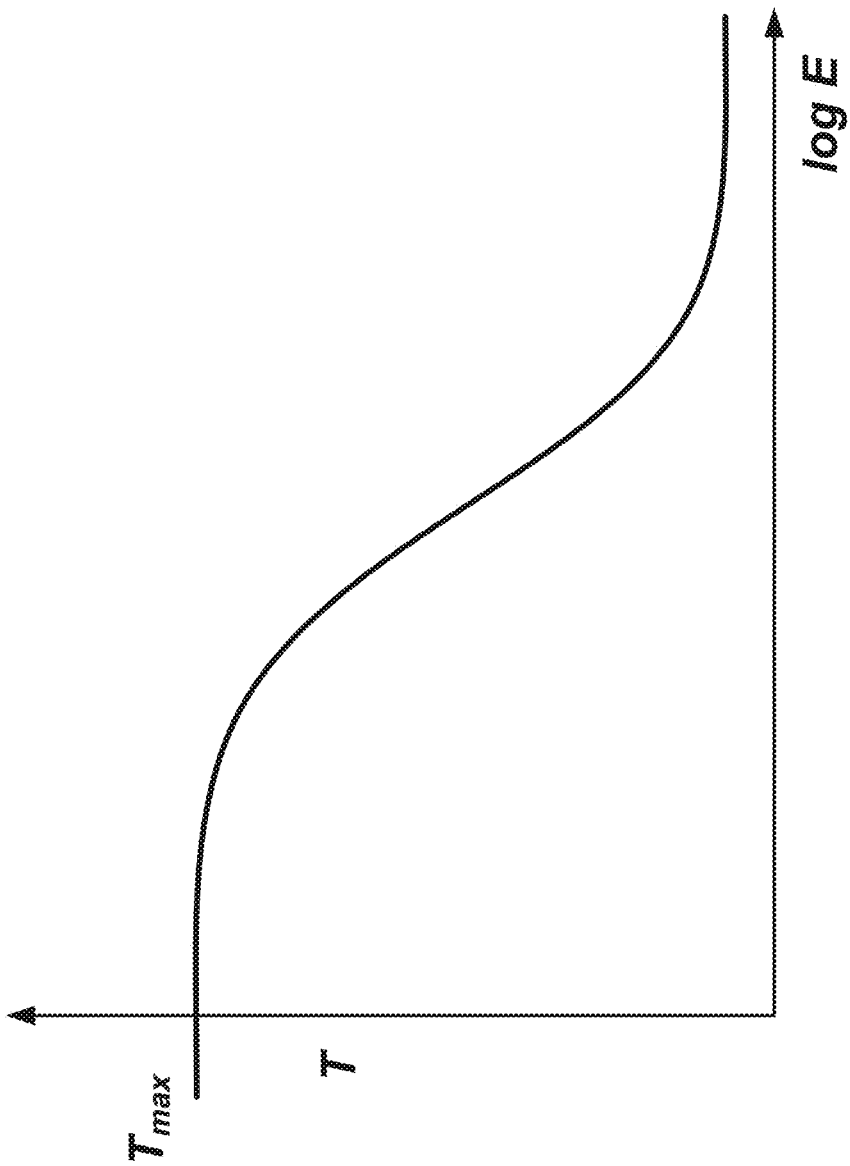
FIG. 16 is a graph representing film transparency as a function of exposure to x-ray radiation.

It should be noted that radiographic film has a minimum density, designated $D_{min}$ in FIG. 15, with $D_{min}$ being greater than zero. Thus, all pixels of radiographic film reduce the brightness of the underlying light box. Put more simply, the film images are dimmer than the bare light box.

In some situations it is desirable for the digital display to accurately mimic only some aspects of actual film on an actual light box, and to mimic other aspects less accurately, e.g., to simplify the computations, avoid the need for collecting accurate data for modeling the film or light box, to modify the display in a manner that improves diagnostic usefulness, or for other reasons.

In some applications, it may be convenient to represent the film 40 by having the user interface module 26 modify the alpha code value associated with each pixel of the image 40. Typically, higher alpha code values represent greater transparency, which is equivalent to lower optical density of film. Therefore, the user interface module 26 modifies the alpha codes of at least some of the pixels of the image 40 to make the image 40 more transparent (i.e., increase its opacity or degree to which the background or other objects are visible through an object in the foreground). It should be understood that reducing the opacity of a digital image as described in the present application does not necessarily make the object brighter, as it would if the opacity of real-world film were affixed to a light box. Although in some cases it has the physical effect of adjusting the contrast, adjusting the opacity of a digital image actually moves the brightness or color of particular pixels a little closer to that of the image or other object behind it.

In some embodiments, the user interface module 26 also modifies the tone scale of a digital image 40. The tone scale of a film-based image, often called the D log E curve by film experts, depends on the particular film used. Usually, the tone scale of a digital image 40 is different from the tone scale of a film-based image. Therefore, the user interface module 26 can modify a digital image 40 to more closely resemble a film-based image by mapping alpha code values, or red/green/blue code values, of the digital image 40 through a compensatory tone scale curve. The compensatory tone scale curve can combine the tone scale of a particular film being imitated with compensation for the tone scale of the original digital image 40. The resulting modified digital image 40 has a tone scale that more closely resembles film tone scale. Accordingly, in some embodiments, the user interface module 26 measures or estimates the tone scale of both the film being imitated and the digital image 40. Alternatively, in other embodiments, accurate reproduction of the film tone scale may be unnecessary or undesirable, and an alternative image tone scale may be used. In some embodiments, simply imposing a maximum brightness of the x-ray images corresponding to the $D_{min}$ of a radiographic film may be used as a tone scale.

It should be understood that not all images span the entire range of a tone scale. Therefore, not all images will have pixels at $D_{min}$ after tone scale correction. For example, a film-based image of a tooth that includes a large metal filling but only natural biological components in the rest of the image, will typically display the filling at densities near $D_{min}$. This occurs because the filling is highly opaque to the x-rays. Therefore, the corresponding spot on the film receives negligible exposure. However, a film-based image of the same tooth prior to inserting the filling typically includes no portion at densities near because nothing in the tooth is sufficiently opaque to x-rays to fully block exposure of the film.

X-ray film also tends to be fairly neutral in color, and digital x-ray images are usually grayscale (i.e., not color). Some film, however, does have a color tint, such as slightly blue. Therefore, in some embodiments, the user interface module 26 is configured to modify a digital image 40 to give the appearance of either a neutral or a tinted film. For example, the user interface module 26 can add a tint to a digital image while keeping non-image areas of the image 40 non-tinted (e.g., white). Similarly, the user interface module 26 can modify the sharpness of the digital image 40 to better match the sharpness of the simulated film. For example, the user interface module 26 can sharpen a digital image 40 by applying to the image 40 a mathematical function such as, for example, a convolution with a sharpening or blurring kernel.

A digital x-ray image may also have different noise characteristics than the x-ray film being simulated. Accordingly, the user interface module 26 can be configured to increase or decrease the noise of the digital image 40 to better simulate the film. The user interface module 26 may add noise in different ways. For example, film-based images typically have noise from several sources: photon shot noise of the x-rays used to create the image (and visible light photons coming from a scintillator simulated by the x-rays) and granularity of the film. Photon shot noise may be represented by Poisson statistics. Therefore, the user interface module 26 can add photon shot noise to a digital image 40 by applying a Poisson random number generator to the digital image 40. The user interface module 26 can also add noise caused by film granularity to the digital image based on the film granularity specified by the film manufacturer of the imitated film. Also, in some embodiments, if the digital image is already noisier than the simulated film image, the user interface module 26 may reduce the noise in the digital image either by low-pass filtering (such as blurring with a convolution kernel or applying a blur filter in Fourier space) or by other noise reduction algorithms.

Some film-based images are mounted on a black mask background. When the film is placed on a light box, only the areas outside of the mask are white. Therefore, in some embodiments, the user interface module 26 modifies a digital image 40 to replicate the black mask and white exterior areas.

In some embodiments, the user interface module 26 also uses characteristics of a digital image 40 to modify the background image 209. For example, while a bright white background may be familiar for users accustomed to light boxes, a bright white background is not always ideal for viewing details within an image. Therefore, the user interface module 26 can create a "feel" of a bright white light box by making the intensity of the background image 209 lower than the brightest area of the image(s) displayed with the background image 209. Accordingly, the user interface module 26 makes the background image 209 as bright as necessary given the brightness of the digital images 40 displayed with the image 209.

The digital image may be viewed under different conditions than actual film on a light box. For example, film on a light box often is viewed in a darkened room, while a digital display is often viewed in a brightly lit room. The "surround," i.e., everything visible outside of the display, affects the observer's perception of the displayed image. Effects such as bright surround and chromatic adaptation are well known. (See, for example, the book "The Reproduction of Colour" by R. W. G. Hunt.) When the digital display is viewed in a different surround than is typical for the imitated light box, the digitally displayed image may be further modified to compensate for the surround, so as to more accurately give the impression of a light box viewed in its normal surround. For example, the contrast may be adjusted when the digital display surround is brighter than the normal light box surround.

It should be understood that although multiple different ways for modifying a digital image 40 are described above, the user interface module 26 may be configured to perform all, a subset, or none of the above modifications. For example, the user interface module 26 may only perform some of the above modifications depending on the desired tradeoff between accurately resembling a light box presentation and standard digital image presentation. The user interface module 26 may also increase or decrease the resemblance of the GUI 41 to a light box presentation either continuously or in several steps. For example, the user interface module 26 can be configured to continuously decrease the resemblance of the GUI 41 to a light box presentation to transition a user who is initially most comfortable with traditional film viewing to standard digital image presentation.

It should also be understood that in some situations few, if any, of the image modifications described above may be applied to enhance the viewing experience. For example, if the digital x-ray image is inherently sharper than images on the simulated film, reducing the digital image sharpness may better resemble the film image but it also reduces image quality. Therefore, the user interface module 26 may not reduce the sharpness of the digital image 40 in these situations. Similarly, the user interface module 26 may set the tone scale of the digital image 40 differently than the tone scale of the simulated film because it improves the diagnostic usefulness of the digital image 40. As another example, the user interface module 26 may reduce the brightness of the light box effect surrounding displayed digital image(s) 40 because too bright a background can impair viewing of the images 40.

Returning to FIG. 6, after modifying the one or more digital images 40 to be displayed with the background image 209, the user interface module 26 generates a final image 211 (at 212). The final image 211 is the result of combining the modified digital image(s) with the background image 209. For example, in some embodiments, the user interface module 26 multiplies the values of the two images pixel-by-pixel to create the final image 211 (e.g., if the alpha code values of the x-ray image represent transparency). The user interface module 26 can also normalize the final image 211 (e.g., based on how brightly the image should be displayed within the brightness limitations of the screen 38). After generating the final image 211, the user interface module 26 sends the final image 211 to the screen 38 for display within the GUI 41 (at 214).

Figure 9:
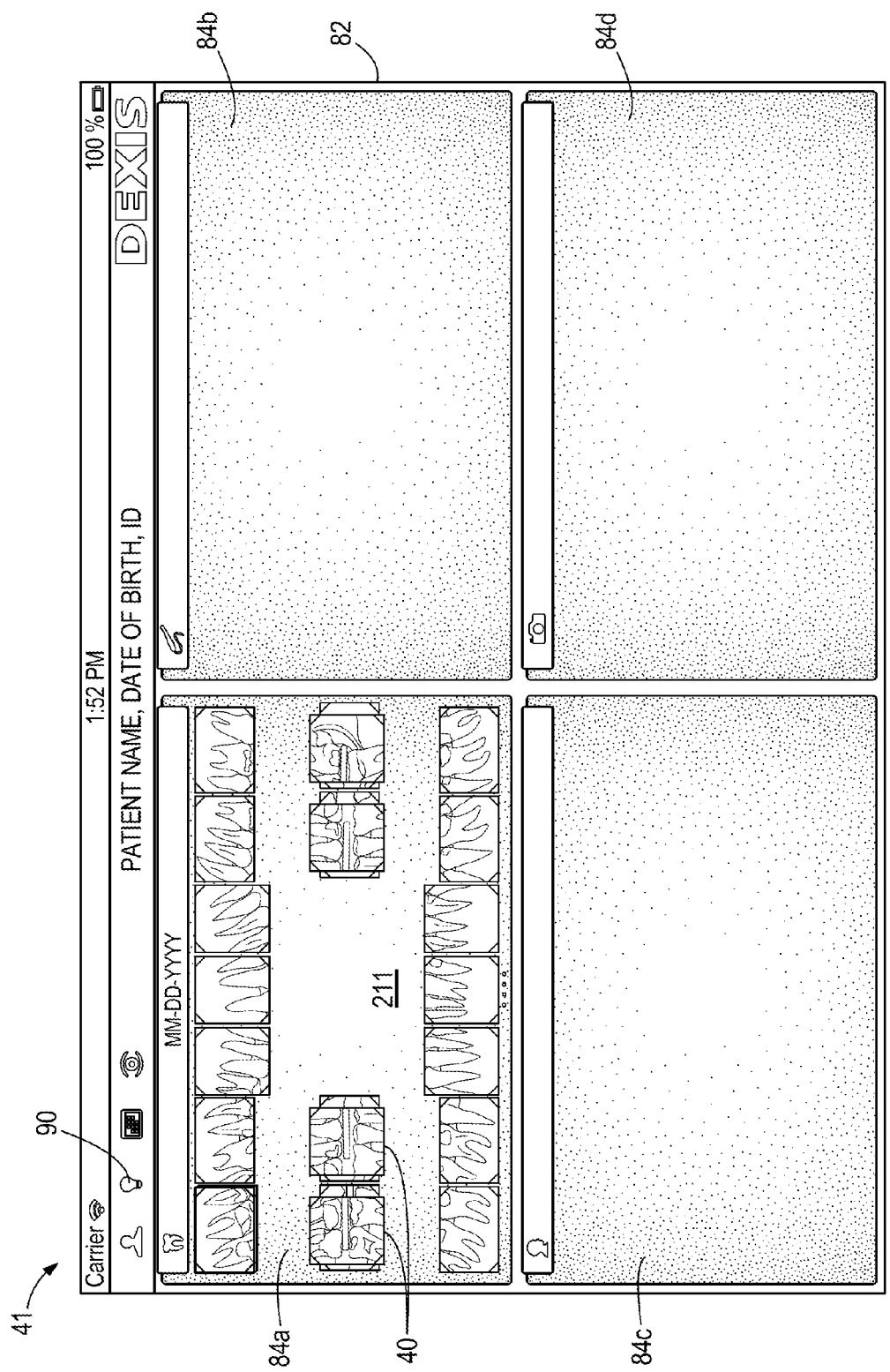
Figure 10:
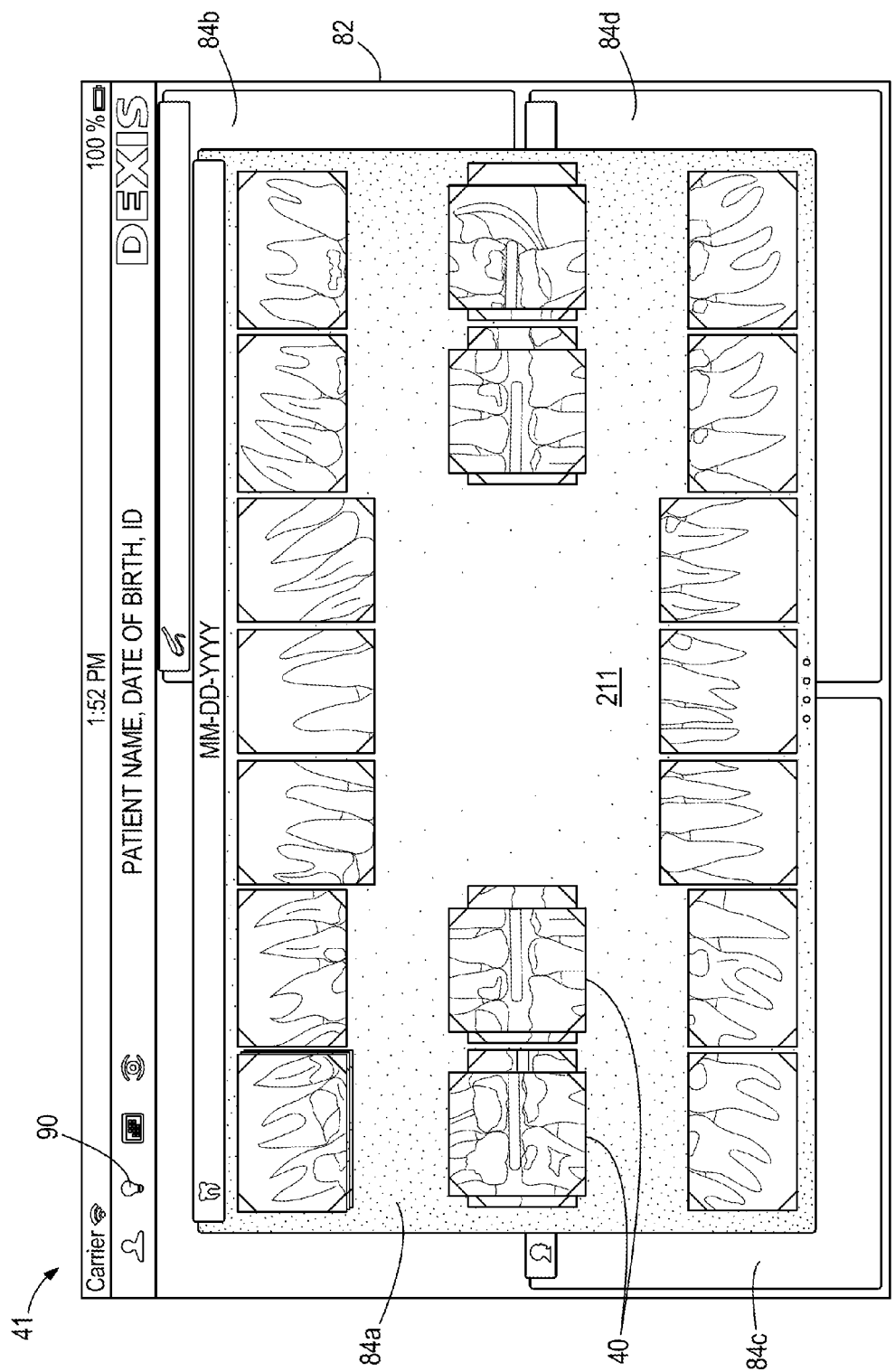
Figure 11:
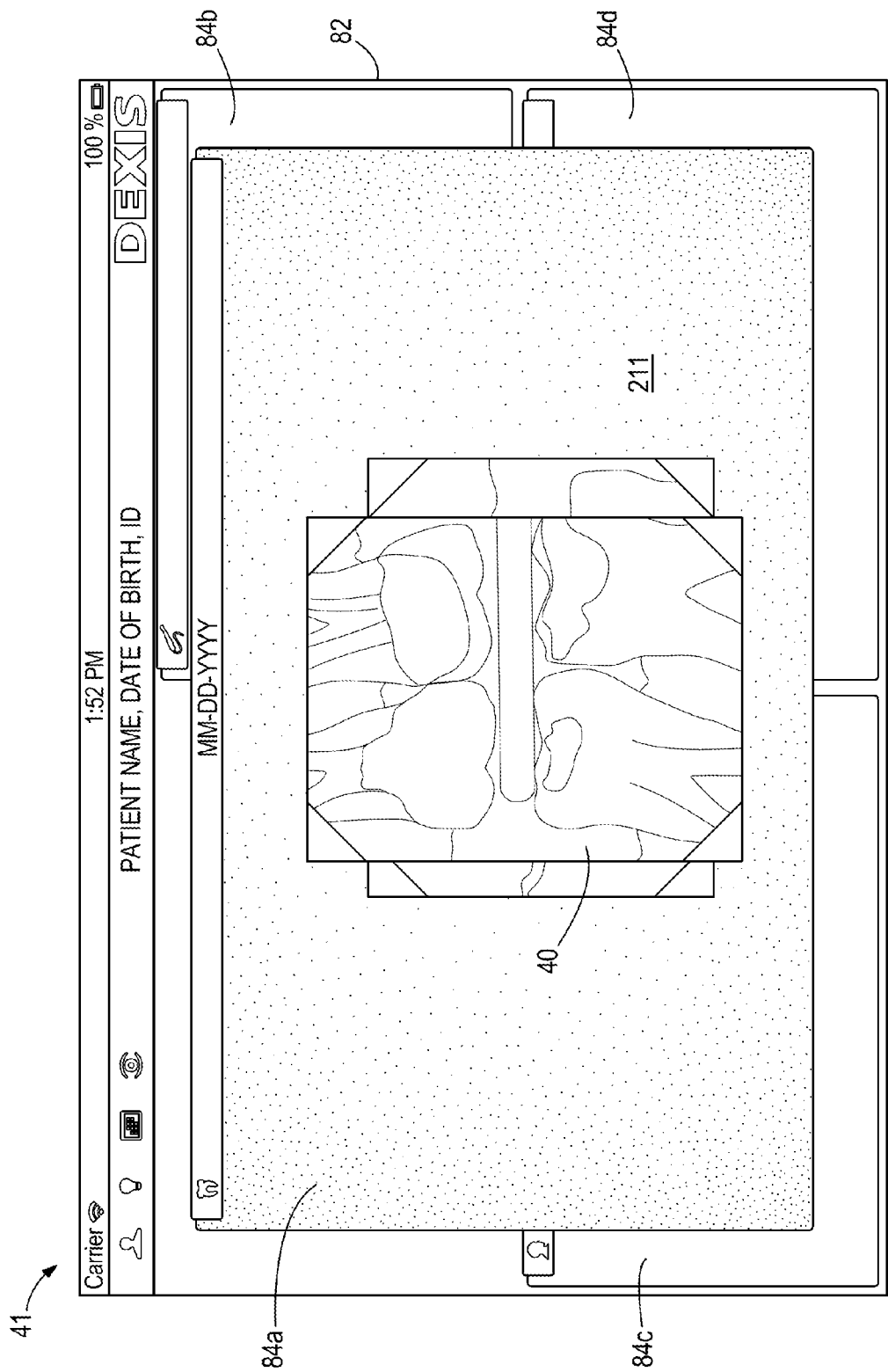

As illustrated in FIG. 9, a final image 211 is displayed in one or more of the panes 84. Furthermore, as illustrated in FIGS. 10-11, the final image 211 can be displayed in an overview mode or a single image mode to provide a user with enlarged or zoomed images displayed with a simulated light box effect. As illustrated in FIGS. 9-11, the light box effect provides a bright region surrounding at least one digital radiographic image 40 to provide a backlighting effect of a displayed digital image 40.

As explained above, a user may view the light box effect displayed in the GUI 41 under different conditions than the user would view actual film on a light box. In particular, a user typically views film on a light box in a darkened room. However, a user may use the computer 30 to view digital images in a well-lit or brightly-lit environment. Human vision adapts according to the surroundings (e.g., brightness and color).

Therefore, just as film images on a light box may appear different when viewed in bright surroundings as opposed to dark surroundings, a digital image 40 may appear different when viewed in bright surroundings as opposed to dark surroundings. For example, in some situations, the apparent contrast of a displayed digital image changes depending on whether the image is viewed in bright surroundings or dark surroundings.

In some embodiments, the light box effect is adjusted based on the surroundings of the user. For example, the ambient light sensor 45 coupled to the computer 30 can be used to automatically determine when to turn on the light box effect and specific parameters for the light box effect to closely resemble a light box presentation viewed in dark surroundings. In particular, as illustrated in FIG. 6, even if a user does not turn on the light box effect by selecting the light box toggle button 90 (at 204), the ambient light sensor 45 can be configured to measure or detect the ambient light around the computer 30 (or, more particularly, around the screen 38) (at 220). The ambient light sensor 45 outputs a signal indicating the amount of light detected around the computer 30. If the signal indicates that the detected ambient light is less than a predetermined darkness threshold (at 222), the user interface module 26 automatically turns on the light box effect (at 206). In some embodiments, the user interface module 26 can also be configured to automatically turn off the light box effect, such as when the ambient light sensor 45 indicates that there is sufficient ambient light for viewing the images 40 in the default mode.

Figure 12:
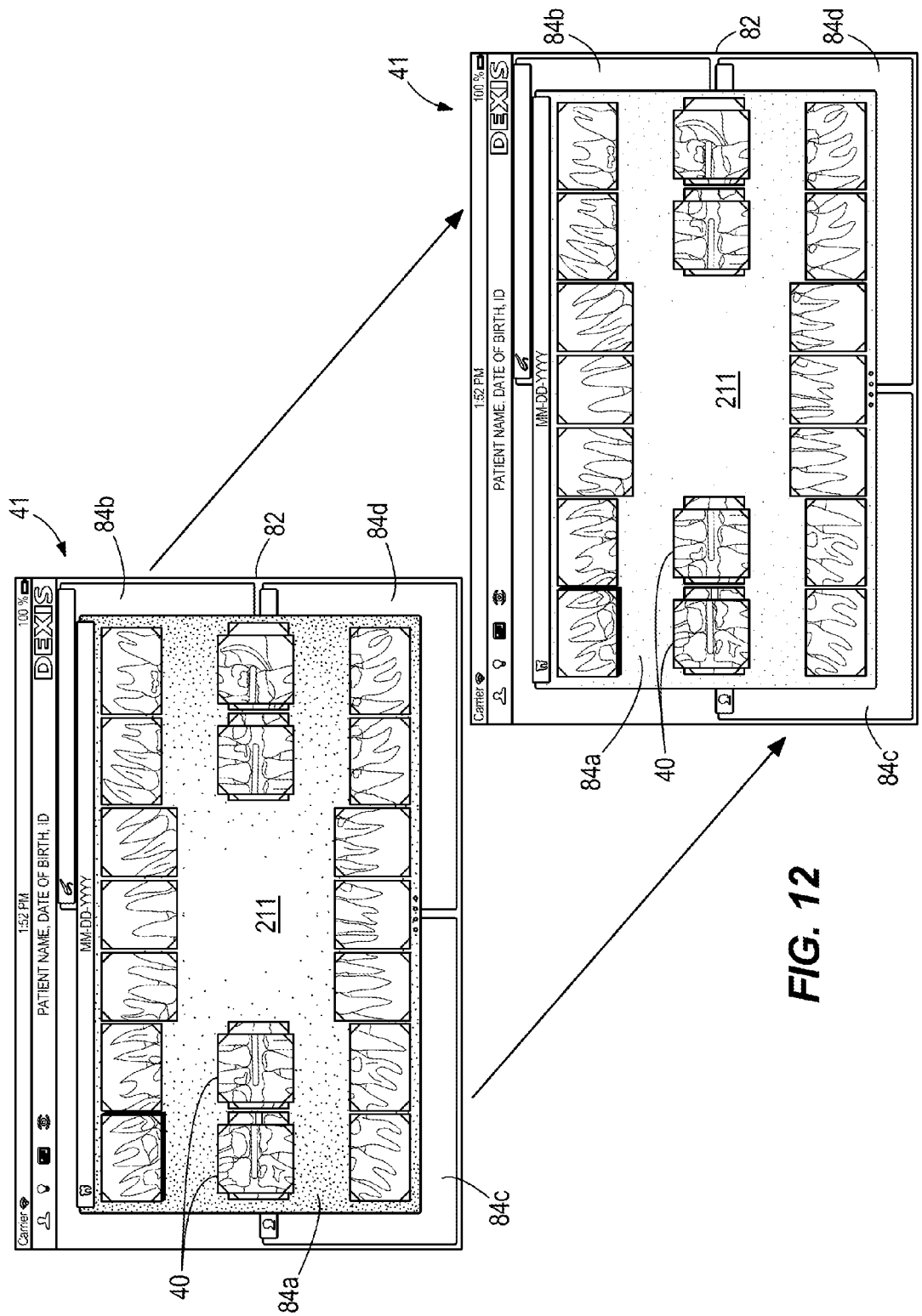

Similarly, after the light box effect is turned on (either manually or automatically), the light box effect can be adjusted (e.g., to account for the user's surroundings). For example, as illustrated in FIG. 6, a user can manually adjust the light box effect (at 230) using various buttons or inputs provided by the GUI 41 or as part of the screen 38. In particular, a user can adjust (e.g., increase or decrease) the opacity of the digital images 40 displayed in the GUI 41 (at 232). Adjusting the opacity of an image can include adjusting the image's contrast and/or transparency. A user can also adjust (e.g., increase or decrease) the brightness of the simulated light box effect (at 234). In some embodiments, the user interface module 26 adjusts both the opacity of the digital images 40 and the brightness of the simulated light effect based on a single adjustment from the user (e.g., increasing or decreasing the brightness of the simulated light box effect). FIG. 12 illustrates the GUI 41 adjusted to increase the opacity of the digital images 40 and to increase the brightness of the simulated light box effect.

As illustrated in FIG. 6, the ambient light sensor 45 can also be used to automatically adjust the light box effect (e.g., in addition to manual adjustments or as an alternative). In particular, the ambient light sensor 45 detects the ambient light around the computer 30 (or, more particularly, around the screen 38) and outputs a signal indicating the amount of light detected around the computer 30 (at 240). The user interface module 26 obtains the signal from the sensor 45 and uses the signal to automatically adjust the simulated light box effect. In particular, based on the detected ambient light, the user interface module 26 adjusts (e.g., increases or decreases) the opacity of the digital images 40 displayed in the GUI 41 (at 242) and/or adjusts (e.g., increases or decreases) the brightness of the simulated light box effect (at 244). Therefore, the ambient light sensor 45 can be used to provide optimal viewing conditions of the image 40 (e.g., higher brightness values in bright ambient situations and lower brightness values in dimmed situations). It should be understood that in some embodiments, a user can turn on and off automatic light box presentation and/or adjustment based on ambient light detected by the ambient light sensor 45.

As illustrated in FIG. 6, a user can manually turn off the light box effect by selecting the light box toggle button 90 (at 230). When the user turns off the light box effect, the user interface module 26 returns the GUI 41 to the default mode (at 202). In some embodiments, the user interface module 26 also saves any settings (e.g., any modified settings) for the light box effect selected or modified by the user (at 250). The user interface module 26 can use the saved settings to default the light box effect to the latest user-defined settings (e.g., brightness) levels the next time the light box mode is turned on. Thus, the invention provides, among other things, devices and systems for creating a graphical user interface for displaying images with a light box effect. Even when the light box effect is not in use, ambient light sensor 45 or user input may be used to determine ambient light levels surrounding the display and adjust the image display accordingly, for example modifying the contrast to compensate for human visual adaptation to the surround as described above.

Although the foregoing has primarily emphasized the use of the invention with human intra-oral images, the invention can also be used with other kinds of images, including but not limited to panoramic and/or cephalometric x-ray images of humans or animals.

Various features and advantages of the invention are set forth in the following claims.

What is claimed is:

1. A device for presentation of digital radiographic images, the device comprising:
   a memory configured to store at least one radiographic image;
   a processor connected to the memory; and
   a user interface module, the user interface module configured to generate a graphical user interface and to cause the at least one radiographic image to be displayed on a display in a first mode and in a light box mode that simulates the appearance of a physical light box, wherein the graphical user interface includes, in the light box mode, a bright region at least partially surrounding the at least one radiographic image and wherein the graphical user interface includes, in the first mode, a dark region at least partially surrounding the at least one radiographic image.

2. The device as claimed in claim 1, wherein, in the light box mode, the bright region at least partially surrounding the at least one radiographic image has a non-uniform brightness.

3. The device as claimed in claim 1, wherein the user interface module is configured to change from the first mode to the light box mode in response to at least one of user input and an output of an ambient light sensor.

4. The device as claimed in claim 1, wherein the at least one radiographic image includes an image of part of a human or animal body.

5. The device as claimed in claim 4, wherein the parts of a human or animal body include teeth.

6. The device as claimed in claim 1, wherein the at least one radiographic image includes a first radiographic image and a second radiographic image and wherein the graphical user interface, in the light box mode, is configured to display the first radiographic image with at least one of a different brightness and a different contrast than the second radiographic image.

7. The device as claimed in claim 1, wherein the light box mode includes a first sub-mode and a second sub-mode, wherein the at least one radiographic image comprises a plurality of images, wherein the first sub-mode is configured to display the plurality of images in an overview mode and the second sub-mode is configured to display one of the plurality of images in a single image mode.

8. A device for presentation of digital radiographic images, the device comprising:
   a memory for storing a radiographic image; and
   a computer connected to the memory, the computer including a processor and a user interface module, the user interface module configured to generate a graphical user interface and to display the radiographic image in the graphic user interface in a first mode and to display the radiographic image in the graphical user interface in a light box mode that includes simulated backlighting of the radiographic image, wherein the computer is configured to change from the first mode to the light box mode in response to at least one of the group consisting of a user input and the output of an ambient light sensor crossing a darkness threshold; and
   a display connected to the computer and configured to display the graphical user interface.

9. The device as claimed in claim 8, wherein the user interface module is configured to adjust the brightness of the simulated backlighting in the light box mode in response to the user input.

10. The device as claimed in claim 8, wherein the user interface module is configured to adjust an opacity of the radiographic image in response to the user input.

11. The device as claimed in claim 8, wherein the graphical user interface includes, in the light box mode, a bright region at least partially surrounding the radiographic image.

12. The device as claimed in claim 8, wherein the graphical user interface includes, in the first mode, a dark region at least partially surrounding the radiographic image.

13. The device as claimed in claim 8, wherein the radiographic image comprise an image of part of a human or animal body.

14. The device as claimed in claim 13, wherein the parts of a human or animal body include teeth.

15. The device as claimed in claim 8, wherein the user interface module is further configured to display a second radiographic image and wherein the graphical user interface, in the light box mode, is configured to display the radiographic image with at least one of a different brightness and a different contrast than the second radiographic image.

16. The device as claimed in claim 8, wherein the light box mode includes a first sub-mode and a second sub-mode, wherein the first sub-mode is configured to display a plurality of radiographic images in an overview mode and the second sub-mode is configured to display the radiographic image in a single image mode.

17. A method of displaying radiographic images, the method comprising:
   storing a radiographic image in a memory;
   connecting a computer to the memory, the computer including a processor and a user interface module;
   connecting a display to the computer;
   generating a graphical user interface using the user interface module and displaying the graphical user interface on the display;
   displaying the radiographic image in the graphic user interface in a first mode; and
   displaying the radiographic image in the graphical user interface in a light box mode that includes simulated backlighting of the at least one radiographic image.

18. The method of claim 17, furthering comprising changing from the first mode to the light box mode in response to at least one of the group consisting of a user input and the output of an ambient light sensor crossing a darkness threshold.

* * * * *